United States Patent
Sacha et al.

(10) Patent No.: US 11,463,827 B2
(45) Date of Patent: Oct. 4, 2022

(54) HEARING DEVICE INCLUDING A SENSOR AND A METHOD OF FORMING SAME

(71) Applicant: Starkey Laboratories, Inc., Eden Prairie, MN (US)

(72) Inventors: Michael K. Sacha, Chanhassen, MN (US); Christopher D. Young, Shorewood, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 17/034,925

(22) Filed: Sep. 28, 2020

(65) Prior Publication Data

US 2021/0014619 A1    Jan. 14, 2021

Related U.S. Application Data

(63) Continuation of application No. 15/799,064, filed on Oct. 31, 2017, now abandoned.

(51) Int. Cl.
*H04R 25/00* (2006.01)
*A61B 5/369* (2021.01)
(Continued)

(52) U.S. Cl.
CPC .......... *H04R 25/556* (2013.01); *A61B 5/369* (2021.01); *A61B 5/389* (2021.01); *A61B 5/398* (2021.01);
(Continued)

(58) Field of Classification Search
CPC ....... G02C 11/06; A61B 5/0533; A61B 5/369; H04R 2225/025; H04R 2225/77;
(Continued)

(56) References Cited

U.S. PATENT DOCUMENTS 5,487,012 A  *  1/1996  Topholm .............. H04R 25/652
                                                        700/163
5,533,130 A      7/1996  Staton
(Continued)

FOREIGN PATENT DOCUMENTS

DE    102005020118    8/2006
EP         1829419    9/2007
(Continued)

OTHER PUBLICATIONS

WO/2007/147406 Housing for a Hearing aid, and method of preparing a hearing aid. English Translation. (Year: 2007).*

*Primary Examiner* — Phylesha Dabney
(74) *Attorney, Agent, or Firm* — Mueting Raasch Group (57) ABSTRACT

Various embodiments of a hearing device and a method of forming such device are disclosed. The device includes a housing adapted to be worn on or behind an ear of a wearer and includes a housing body and a top plate connected to the housing body. The hearing device further includes a sensor disposed on at least one of a first side surface and a second side surface of the housing body. The sensor is adapted to be in contact with either a pinna or a skull of the wearer. The sensor is further adapted to detect a physiological characteristic of the wearer and generate a sensor signal based on the physiological characteristic.

19 Claims, 7 Drawing Sheets

(51) Int. Cl.
*A61B 5/389* (2021.01)
*A61B 5/398* (2021.01)
*H04R 25/02* (2006.01)
*H04R 31/00* (2006.01)
*G02C 11/06* (2006.01)
*A61B 5/0533* (2021.01)

(52) U.S. Cl.
CPC ........... *H04R 25/02* (2013.01); *H04R 25/554* (2013.01); *H04R 25/60* (2013.01); *H04R 25/65* (2013.01); *H04R 31/00* (2013.01); *A61B 5/0533* (2013.01); *G02C 11/06* (2013.01); *H04R 25/603* (2019.05); *H04R 25/607* (2019.05); *H04R 25/658* (2013.01); *H04R 2225/025* (2013.01); *H04R 2225/77* (2013.01)

(58) Field of Classification Search
CPC .... H04R 25/02; H04R 25/554; H04R 25/556; H04R 25/60; H04R 25/65; H04R 25/658; H04R 31/00; H04R 2225/021; H04R 25/603; H04R 25/607
USPC .......................................................... 381/324
See application file for complete search history.

(56) References Cited

U.S. PATENT DOCUMENTS

| | | |
|---|---|---|
| 7,103,192 B2 | 9/2006 | Bailey |
| 7,450,730 B2 | 11/2008 | Berg et al. |
| 8,652,040 B2 | 2/2014 | Leboeuf et al. |
| 8,866,661 B2 | 10/2014 | Knudsen et al. |
| 9,210,517 B2 | 12/2015 | Pontoppidan et al. |
| 9,723,396 B2 | 8/2017 | Qian et al. |
| 2003/0133583 A1 | 7/2003 | Widmer et al. |
| 2008/0165017 A1 | 7/2008 | Schwartz |
| 2011/0137141 A1 | 6/2011 | Razoumov et al. |
| 2013/0343584 A1 | 12/2013 | Bennett et al. |

FOREIGN PATENT DOCUMENTS

| | | |
|---|---|---|
| EP | 2448477 | 5/2012 |
| WO | 2007/147406 | 12/2007 |
| WO | 2011/038767 | 4/2011 |
| WO | 2011/091856 | 8/2011 |

\* cited by examiner

FIG. 12

HEARING DEVICE INCLUDING A SENSOR AND A METHOD OF FORMING SAME

RELATED PATENT DOCUMENTS

This application is a continuation of U.S. application Ser. No. 15/799,064, filed Oct. 31, 2017, which is incorporated herein by reference in its entirety.

BACKGROUND

Hearing devices, such as hearing aids, can be used to transmit sounds to one or both ear canals of a wearer. Some hearing devices can include electronic components disposed within a housing that is placed in a cleft region that resides between an ear and a skull of the wearer. Such housings typically can be connected to an earpiece that is disposed in an ear canal of the ear of the wearer.

For hearing assistance devices such as hearing aids, a behind-the-ear (BTE) hearing aid can utilize tubing or wires that connect the housing of the hearing aid to the earpiece disposed in the ear. The housing can include a rectangular cross-section and a curved shape that can follow a contour of the cleft region between the ear and the skull of the wearer.

Further, body-worn devices can include one or more sensors that can measure one or more physiological characteristics of the wearer. For example, devices worn on the wrist or chest can be utilized to measure a heart rate of the wearer. Further, finger-worn devices can be utilized to measure the oxygen content of blood of the wearer. These one or more sensors can be disposed in any suitable location on the wearer's body. For example, a hearing device can include a sensor disposed on a housing of the device. Such sensor can be in contact with the body of the wearer and can be utilized to measure a physiological characteristic of the wearer.

SUMMARY

In general, the present disclosure provides various embodiments of a hearing device and a method of forming such device. The hearing device can include a housing, electronic components disposed within the housing, and one or more sensors disposed on a surface of the housing. A sensor of the one or more sensors can be adapted to detect a physiological characteristic of a wearer of the hearing device and generate a sensor signal based on the physiological characteristic.

In one aspect, the present disclosure provides a hearing device that includes a housing adapted to be worn on or behind an ear of a wearer and that extends along a housing axis, the housing including a substantially triangular cross-section in a plane orthogonal to the housing axis. The housing further includes a housing body and a top plate connected to the housing body, where the housing body includes a first side surface adapted to be disposed adjacent a pinna of the ear of the wearer and a second side surface adapted to be disposed adjacent a skull of the wearer. The first and second side surfaces are connected to one another at a bottom edge of the housing body. The hearing device further include electronic components disposed within the housing, where the electronic components includes a controller; and a sensor disposed on at least one of the first and second side surfaces of the housing body and electrically coupled to the controller, where the sensor is adapted to be in contact with either the pinna or the skull of the wearer, and where the sensor is further adapted to detect a physiological characteristic of the wearer and generate a sensor signal based on the physiological characteristic. The hearing device further includes an earpiece adapted to be disposed in an ear canal of the ear of the wearer, where the earpiece is operatively coupled to the electronic components disposed within the housing.

In another aspect, the present disclosure provides a method of forming a hearing device. The method includes forming a three-dimensional model of a cleft region between a pinna and a skull of a wearer, forming a three-dimensional model of a housing of the hearing device based upon the three-dimensional model of the cleft region, and forming a housing of the hearing device based upon the three-dimensional model of the housing.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure provides various embodiments of a hearing device and a method of forming such device. The hearing device can include a housing, electronic components disposed within the housing, and one or more sensors disposed on a surface of the housing. A sensor of the one or more sensors can be adapted to detect a physiological characteristic of a wearer of the hearing device and generate a sensor signal based on the physiological characteristic. In one or more embodiments, the housing can have a substantially triangular-shaped cross-section.

Currently-available hearing devices that are disposed behind an ear of a wearer may not conform to the wearer's anatomy. For example, a typical behind-the-ear (BTE) hearing devices include a housing that has a rectangular cross-section in a plane that is orthogonal to a skull of the wearer. Such rectangular cross-section does not, however, conform to a cleft region of the wearer that is defined by the space between a skull and a pinna of the ear of the wearer. Although these devices can have a curved shape in a plane parallel to the wearer's head that somewhat follows a curve of the pinna, such rectangular cross-section in an orthogonal plane does not utilize the space that is available in the cleft region.

In contrast to these currently-available devices, one or more embodiments of hearing devices described herein can include a housing that is shaped to better conform to the wearer's ear between the pinna and the skull. Such housing can provide more consistent placement of microphones and antennae associated with the hearing device. Further, the housing can allow for better placement of one or more sensors that can also be included with the hearing device for detecting various physiological characteristics of the wearer. For example, a sensor disposed on or within the housing can have better skin contact with the wearer's ear or skull because the housing has been designed to better conform to the cleft region. This improved skin contact can improve the accuracy of the sensor. Further, the housing can be more stable than housings of currently-available devices as the housing more accurately conforms to the wearer's anatomy. By better utilizing the space of the cleft region, the housing can also have a less conspicuous profile that provides a hearing device that is more discrete. Further, one or more embodiments of hearing devices described herein can include a housing that has an increased interior volume that can allow for additional components to be disposed within the housing, thereby providing additional functionalities to the hearing device.

FIGS. 1-6 are various views of one embodiment of a hearing device 10. The hearing device 10 includes a housing 20 adapted to be worn on or behind an ear of a wearer, electronic components 40 (FIG. 3) disposed within the housing, and a sensor 60 disposed on a housing body 22 of the housing. The device 10 also includes an earpiece 80 adapted to be disposed in an ear canal of the ear of the wearer, where the earpiece is operatively coupled to the electronic components 40 disposed within the housing 20.

Figure 3:
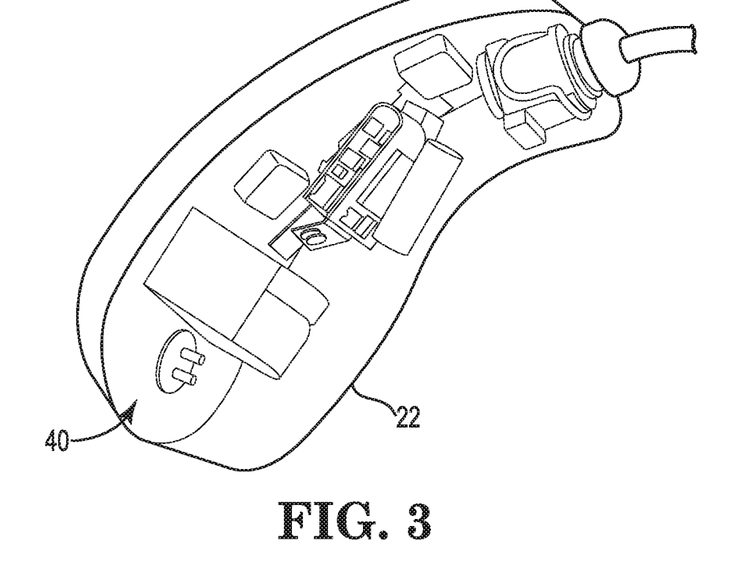
FIG. 3 is a schematic bottom perspective view of the hearing device of FIG. 1.
Figure 4:
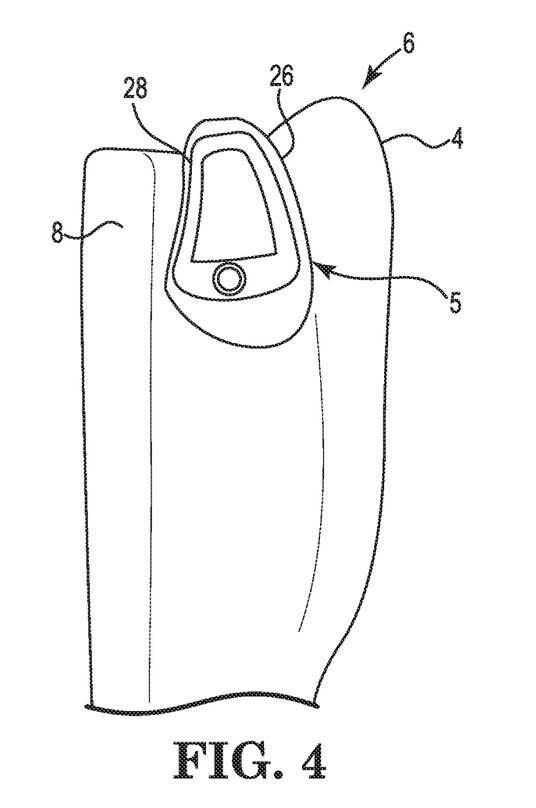
FIG. 4 is a schematic perspective view of the hearing device of FIG. 1 disposed in a cleft region of a wearer.
Figure 5:
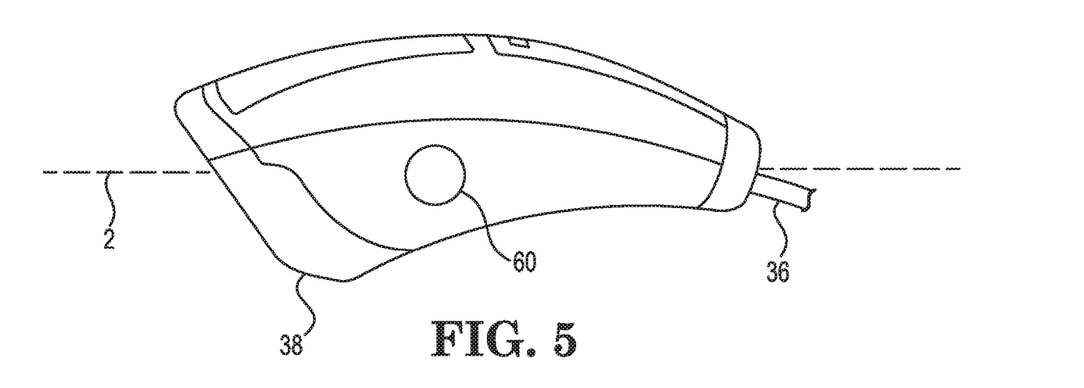
FIG. 5 is a schematic side view of the hearing device of FIG. 1.
Figure 6:
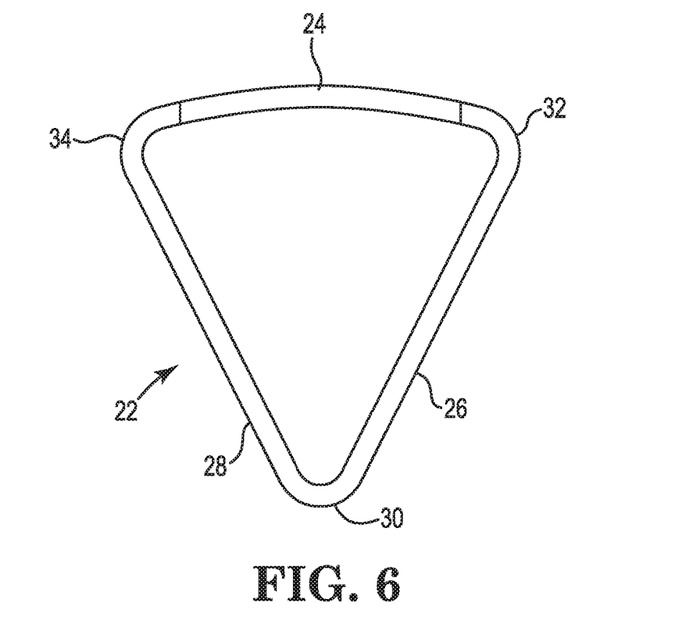
FIG. 6 is a schematic cross-section view of the hearing device of FIG. 1.

The housing 20 extends along a housing axis 2 (FIG. 5). In one or more embodiments, the housing 20 extends along the housing axis 2 between a first end 36 and a second end 38 of the housing. Further, the housing 20 can have any suitable dimensions and take and suitable shape or shapes. For example, in the embodiment illustrated in FIGS. 1-6, the housing 20 has a substantially triangular cross-section (FIG. 6) in a plane orthogonal to the housing axis 2. As used herein, the term "substantially triangular" means that the housing 20 has a cross-section in the plane orthogonal to the housing axis 2 that has three major surfaces that meet at three vertices or edges 30, 32, 34 as shown in FIG. 6.

Figure 12:
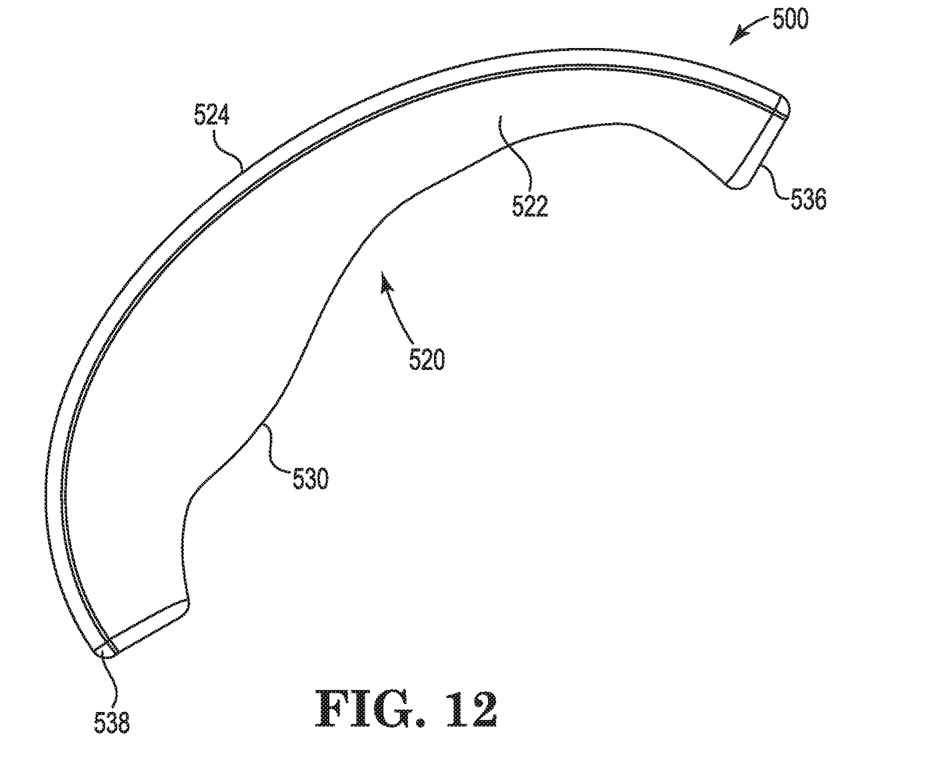
FIG. 12 is a schematic perspective view of another embodiment of a housing of a hearing device.

FIG. 12 is a schematic perspective view of another embodiment of a housing 500 that can be utilized with any suitable hearing device. All of the design considerations and possibilities described regarding the housing 20 of FIGS. 1-6 apply equally to the housing 500 of FIG. 12. The housing 500 includes a housing body 520 and a top plate 524 connected to the housing body. The housing body 520 includes a first side surface 522 and a second side surface (not shown) that are connected to one another at a bottom edge 530 of the housing body. The housing 500 extends between a first end 536 and a second end 538 and can have any suitable length. As can be seen in FIG. 12, the bottom edge 530 has a contoured shape that can conform to a cleft region of a wearer. Further, one or more of the first side surface 522 and the second side surface can also include a contoured shape that conforms to a surface of a pinna and a surface of a skull of the wearer respectively. Such conforming surfaces of the housing body 520 can provide improved contact between a sensor disposed on one or more of the surfaces and the wearer.

Returning to FIGS. 1-6, the housing 20 includes the housing body 22 and the top plate 24 that is connected to the housing body. The housing body 22 includes a first side surface 26 and a second side surface 28. The first side surface 26 is adapted to be disposed adjacent the pinna 4 of the ear 6 of the wearer as shown in FIG. 4. As used herein, the term "adjacent the pinna" means that the first side surface 26 of the housing body 22 is disposed closer to the pinna 4 than to the skull 8 of the wearer. In one or more embodiments, one or more portions of the first side surface 26 are adapted to be disposed in contact with the pinna 4. Further, the second side surface 28 is adapted to be disposed adjacent the skull 8 of the wearer as is also shown in FIG. 4. As used herein, the term "adjacent the skull" means that the second side surface 28 is disposed closer to the skull 8 than to the pinna 4 of the wearer. In one or more embodiments, one or more portions of the second side surface 28 are adapted to be disposed in contact with the pinna 8. The first and second side surfaces 26, 28 are connected to one another at a bottom edge 30 of the housing body 22.

Each of the first side surface 26 and the second side surface 28 can take any suitable shape or shapes. In one or more embodiments, portions of one or both of the first and second side surfaces 26, 28 can take a curved shape. The housing body 22 can be a unitary body such that the first and second side surfaces 26, 28 are integral or continuous. In one or more embodiments, the first and second side surfaces 26, 28 can be manufactured separately and then joined together using any suitable technique or techniques.

Further, the top plate 24 can take any suitable shape or combination of shapes. In one or more embodiments, the top plate 24 includes a curved shape in the plane orthogonal to the housing axis 2 as shown in FIG. 6. In one or more embodiments, the top plate 24 can include a curved shape in a plane parallel to the housing axis 2 and the bottom edge 30 of the housing body as shown in FIG. 5. Further, in one or more embodiments, the top plate 24 can include a first curved shape in the plane orthogonal to the housing axis 2 (FIG. 6) and a second curved shape in the plane parallel to the housing axis 2 and the bottom edge 30 of the housing body 22 (FIG. 5).

Figure 8:
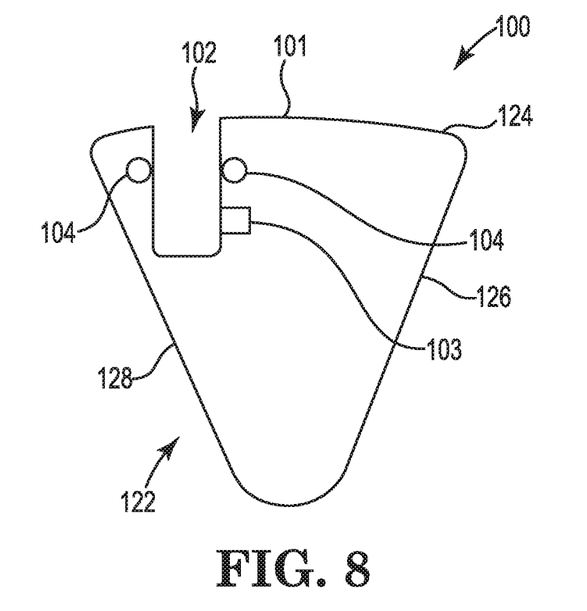
FIG. 8 is a schematic cross-section view of a housing of another embodiment of a hearing device.

The housing 20 can also include one or more recesses or notches to accommodate an arm or bow of the wearer's eyeglasses. For example, FIG. 8 is a schematic cross-section view of another embodiment 100 of a housing 100. All of the design considerations and possibilities regarding the housing 20 of the hearing device 10 of FIGS. 1-6 apply equally to the housing 100 of FIG. 8. The housing 100 includes a notch 102 disposed in an outer surface 101 of a top plate 124. The notch 102 can take any suitable shape and have any suitable dimensions such that it is adapted to receive a bow of a pair of eyeglasses when the eyeglasses are worn by the wearer.

In one or more embodiments, the top plate 124 to can also include one or more contact pads 104 disposed in any suitable location in the notch 102 of the top plate. The contact pads 104 are electrically connected to the electronic components (e.g. electronic components 40 of device 10) disposed within the housing 100. The contact pads 104 are adapted to be electrically connected to one or more contact pads disposed on the bow of the eyeglasses such that a hearing device that includes the housing 100 is electrically connected to the eyeglasses. Although not shown, the housing 100 can also include one or more electromagnetic coils disposed in the housing adjacent the notch 102. As used herein, the term "adjacent the notch" means that an element or component is disposed within the housing 100 closer to the notch 102 than to a side surface 126, 218 of a housing body 122 of the housing. Such electromagnetic coils can be utilized to transmit electromagnetic signals between the hearing device and the eyeglasses. For example, in one or more embodiments, the eyeglasses can include a transceiver that can be positioned adjacent the coils disposed in the housing 100 such that one or more electromagnetic signals can be transmitted between the device and the eyeglasses.

In one or more embodiments, one or more magnetic regions 103 can be disposed within the housing 100 and adjacent the notch 102. Such magnetic regions 103 can magnetically connect the housing 100 to the bow of the eyeglasses utilizing an attractive force such that the bow is retained in the notch. The retention of the bow in the notch 102 by the magnetic region 103 can maintain electrical contact between the contact pads 104 and the bow and also maintain coil alignment between the hearing device and the bow. Any suitable magnetic material or materials can be utilized for magnetic region 103.

Returning to FIGS. 1-6, the top plate 24 is connected to the housing body 22 at a first top edge 32 and a second top edge 34 (FIG. 6). The top edges 32, 34 and the bottom edge 30 can take any suitable shape or shapes. In the embodiment illustrated in FIG. 6, the edges 30, 32, 34 can take a rounded shape. In one or more embodiments, one or more of the edges 30, 32, 34 can take a rectilinear shape such that the edges are not rounded.

The housing 20 can be manufactured utilizing any suitable technique or techniques, e.g., injection-molding, 3D printing, etc. The housing 20 can include any suitable material or materials, e.g., silicone, urethane, acrylates, flexible epoxy, acrylated urethane, and combinations thereof. The housing body 22 can include the same material or materials utilized to form the top plate 24. In one or more embodiments, the housing body 22 can include a material that is different from the material utilized to form the top plate 24.

Figure 9:
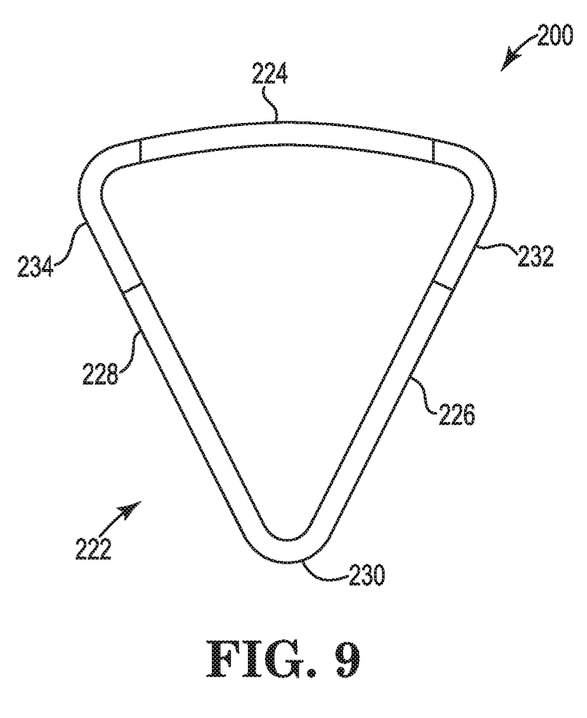
FIG. 9 is a schematic cross-section view of a housing of another embodiment of a hearing device.

For example, FIG. 9 is a schematic cross-section view of another embodiment of a housing 200 that can be utilized with any suitable hearing device, e.g., hearing device 10 of FIGS. 1-6. All of the design considerations and possibilities regarding the housing 20 of hearing device 10 of FIGS. 1-6 apply equally to housing 200 of FIG. 9. The housing 200 includes a housing body 222 and a top plate 224. The housing body 222 includes a first side surface 226 and a second side surface 228 that are connected to one another at a bottom edge 230. Further, the housing 200 includes the top plate 224 connected to the body 222 at first and second top edges 232, 234. The top plate 224 and the first and second side surfaces 226, 228 of the housing body 222 include a first material, and the first and second top edges 232, 234 of the housing body include a second material. In one or more embodiments, the first material is the same as the second material. Further, in one or more embodiments, the first material is different from the second material. For example, the first material can have a hardness that is greater than or less than a hardness of the second material. Although not shown, the bottom edge 230 can include a material that is different from the material utilized to form the side surfaces 226, 228 of the housing body 222. In one or more embodiments, a softer material can be utilized for one or more of the top edges 232, 234 and the bottom edge 230, the housing 200 to provide a more comfortable fit for the wearer.

Returning to FIGS. 1-6, electronic components 40 are disposed within housing 20. The electronic components 40 can be disposed in any suitable location or arrangement within the housing 20. In one or more embodiments, one or more electronic components 40 can be disposed on the top plate 24 and placed within the housing 20 when the top plate is connected to the housing body 22 as shown in FIG. 3, where the body 22 is shown as transparent for illustration purposes.

Figure 7:
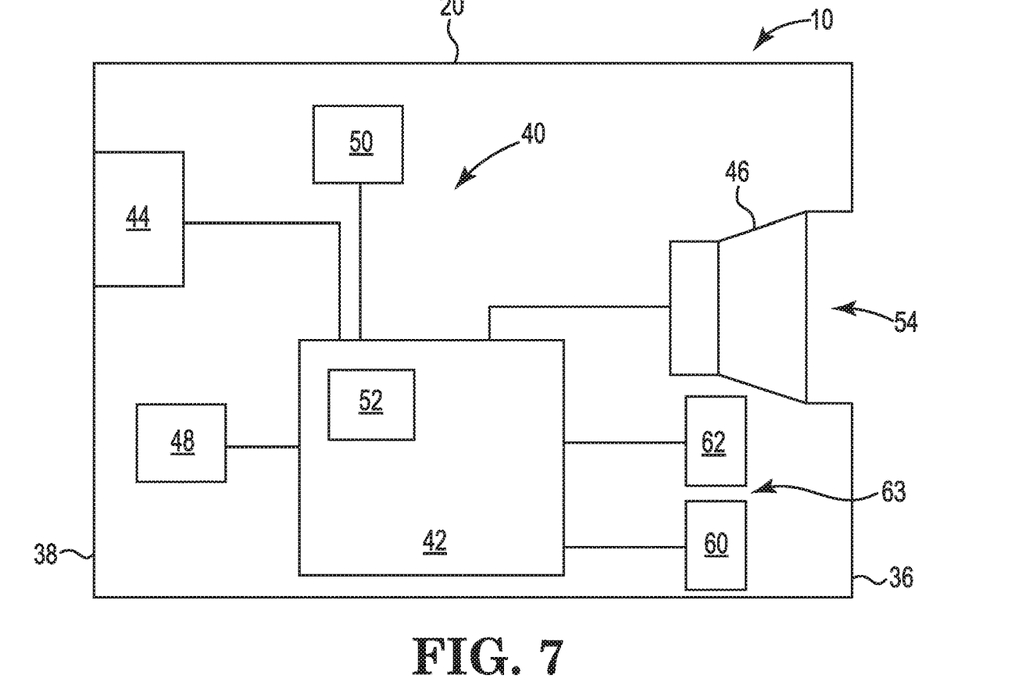
FIG. 7 is a schematic cross-section view of the housing of the hearing device of FIG. 1.

The hearing device 10 can include any suitable electronic component or components. For example, FIG. 7 is a schematic cross-section view of the hearing device 10 of FIGS. 1-6. Electronic components 40 are disposed within the housing 20 of the device 10. The electronic components 40 can include any suitable device or devices, e.g., integrated circuits, power sources, microphones, receivers, etc. For example, in one or more embodiments, the components 40 can include a controller 42, a microphone 44, a receiver 46 (e.g., speaker), a power source 48, an antenna 50, the sensor 60, and a second sensor 62. The microphone 44, receiver 46, power source 48, antenna 50, and sensors 60,62 can be electrically connected to the controller 42 using any suitable technique or techniques.

Any suitable controller 42 can be utilized with the hearing device 10. For example, in embodiments where the hearing device 10 is utilized as a hearing aid, the controller 42 can be adapted to employ programmable gains to adjust the hearing device output to the wearer's particular hearing impairment. The controller 42 can be a digital signal processor (DSP), microprocessor, microcontroller, other digital logic, or combinations thereof. The processing can be done by a single processor or can be distributed over different devices. The processing of signals referenced in this disclosure can be performed using the controller 42 or over different devices.

The processing of signals referenced in this application can be performed using the processor or other different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In one or more embodiments, the controller 42 or other processing devices execute instructions to perform a number of signal processing tasks. Such embodiments can include analog components in communication with the controller 42 to perform signal processing tasks, such as sound reception by the microphone 44, or playing of sound using the receiver 46.

The electronic components 40 can also include the microphone 44 that is electrically connected to the controller 42. Although one microphone 44 is depicted, the components 40 can include any suitable number of microphones. Further, the microphone 44 can be disposed in any suitable location within the housing 20. For example, in one or more embodiments, a port or opening can be formed in the housing 20, and the microphone 44 can be disposed adjacent the port to receive audio information from the wearer's environment.

Any suitable microphone 44 can be utilized. In one or more embodiments, the microphone 44 can be selected to detect one or more audio signals and convert such signals to an electrical signal that is provided to the processor. Although not shown, the controller 42 can include an analog-to-digital convertor that converts the electrical signal from the microphone 44 to a digital signal.

Electrically connected to the controller 42 is the receiver 46. Any suitable receiver can be utilized. In one or more embodiments, the receiver 46 can be adapted to convert an electrical signal from the controller 42 to an acoustic output or sound that can be transmitted from the housing 20 to the wearer. In one or more embodiments, the receiver 46 can be disposed adjacent an opening 54 disposed in the first end 36 of the housing 20. As used herein, the term "adjacent the opening" means that the receiver 46 is disposed closer to the opening 54 in the first end 36 than to the second end 38 of the housing 20. The opening 54 can be connected to an ear hook 84 such that one or both of acoustic and electrical energy can be directed between the housing 20 and the earpiece 80.

The power source 48 is electrically connected to the controller 42 and is adapted to provide electrical energy to the controller and one or more of the other hearing assistance components 40. The power source 48 can include any suitable power source or power sources, e.g., a battery. In one or more embodiments, the power source 48 can include a rechargeable battery. In one or more embodiments, the components 40 can include two or more power sources 48.

The electronic components 40 can also include the optional antenna 50. Any suitable antenna or combination of antennas can be utilized. In one or more embodiments, the antenna 50 can include one or more antennas having any suitable configuration. For example, antenna configurations can vary and can be included within the housing 20 or be external to the housing. Further, the antenna 50 can be compatible with any suitable protocol or combination of protocols. In one or more embodiments, the components 40 can also include a transmitter that transmits electromagnetic signals and a radio-frequency receiver that receives electromagnetic signals using any suitable protocol or combination of protocols.

For example, in one or more embodiments, the hearing device 10 can be connected to one or more external devices using, e.g., Bluetooth, Wi-Fi, magnetic induction, etc. For example, in one or more embodiments, the hearing device 10 can be wirelessly connected to the Internet using any suitable technique or techniques. Such connection can enable the hearing device 10 to access any suitable databases, including medical records databases, cloud computing databases, location services, etc. In one or more embodiments, the hearing device 10 can be wirelessly connected utilizing the Internet of Things (IoT) such that the hearing device can communicate with, e.g., hazard beacons, one or more cameras disposed in proximity to the wearer, motion sensors, room lights, etc.

In embodiments where the hearing device 10 includes a second hearing device disposed on an opposite side of the wearer's head, the antenna 50 can be utilized to communicate with an antenna of the second hearing device. In one or more embodiments, a low-power link across the wearer's head can be utilized to transmit electromagnetic signals between the first and second hearing devices.

In one or more embodiments, the hearing device 10 can include the sensor 60 and the second sensor 62 (collectively the sensors 63). Although depicted as including two sensors 60, 62, the hearing device 10 can include any suitable number of sensors, e.g., 1, 2, 3, 4, 5, or more sensors. The sensors 60, 62 can include any suitable sensor or sensors. The sensor 60 can include the same sensor as the second sensor 62. In one or more embodiments, the sensor 60 includes a sensor that is different from that of the second sensor 62. The sensors 60, 62 can be operatively connected to the controller 42 using any suitable technique or techniques, e.g., electrical, optical, or wireless connections.

In one or more embodiments, sensor 60 is operatively connected to the hearing device 10 and adapted to detect a first physiological characteristic of the wearer and generate a sensor signal based on the first physiological characteristic. Further, the second sensor 62 is operatively connected to the hearing device 10 and adapted to detect a second physiological characteristic of the wearer and generate a second sensor signal based on the second physiological characteristic. The controller 42 can be adapted to receive the sensor signal from the sensor 60 and the second sensor signal from the second sensor 62. The first and second sensor signals can be analyzed by the controller 42 or transmitted by the antenna 50 to a remote controller or controllers for analysis utilizing any suitable technique or techniques.

The first and second physiological characteristics can include any suitable physiological characteristic. The physiological characteristic detected by the sensor 60 can be the same as or different from the second physiological characteristic detected by the second sensor 62. For example, in one or more embodiments, the physiological characteristic detected by the sensor 60 can be a blood pressure of the wearer and the second physiological characteristic detected by the second sensor 62 can be a pulse of the wearer.

The sensors 63 can be disposed in any suitable location. In one or more embodiments, the sensor 60 and the second sensor 62 can be disposed on the same side surface of the housing 20. In one or more embodiments, the sensor 60 can be disposed on the first side surface 26 and the second sensor can be disposed on the second side surface 28. Further, in one or more embodiments, one or more sensors can be disposed on or in the top plate 24.

Figure 1:
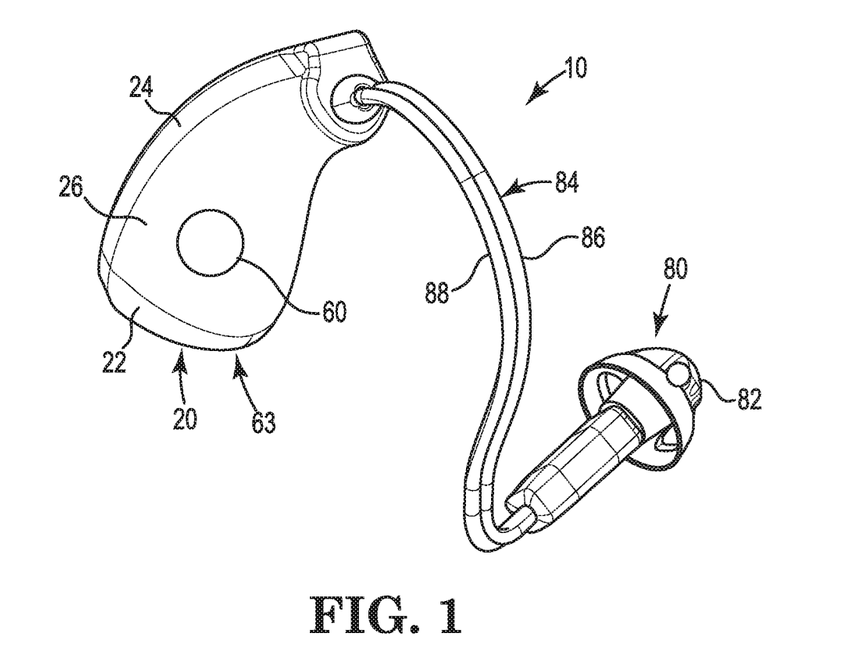
FIG. 1 is a schematic right perspective view of one embodiment of a hearing device that includes a housing and an earpiece operatively connected to the housing.
Figure 2:
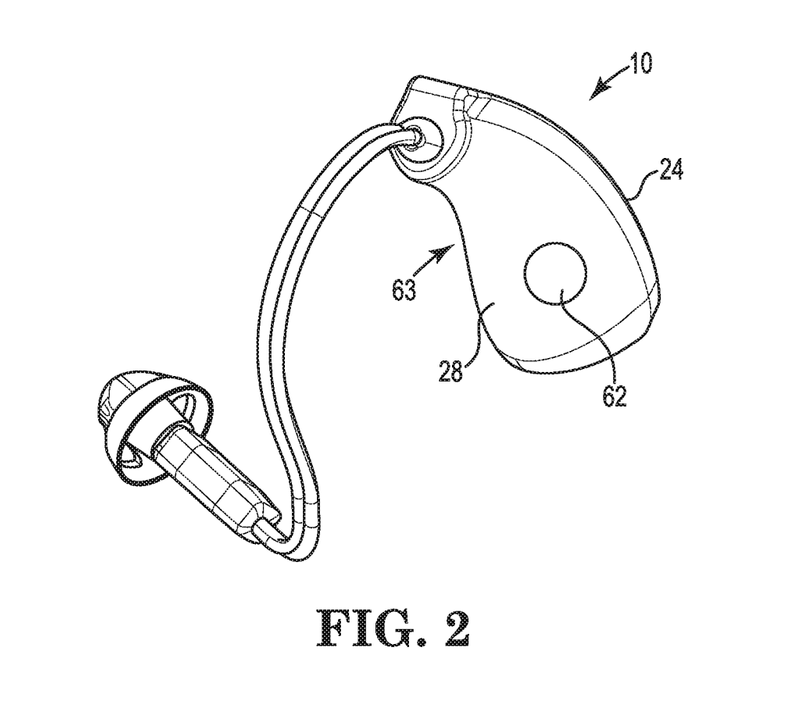
FIG. 2 is a schematic left perspective view of the hearing device of FIG. 1.

In one or more embodiments, one or more sensors 63 can be disposed apart from the housing 20 and operatively coupled to the controller 42 or a remote controller using any suitable technique or techniques. In one or more embodiments, one or more sensors 63 can be disposed within one or both ears and outside the ear of the wearer. For example, earpiece 80 can include one or more sensors 82 as shown in FIG. 1. The sensor 82 can be adapted to detect a physiological characteristic of the wearer and generate a sensor signal based on the physiological characteristic. Any suitable physiological characteristic can be detected by the sensor 82, e.g., the same physiological characteristics detected by sensors 60, 62.

The sensors 63 can include any suitable sensor or sensors, e.g., an electrical sensor, an optical sensor, a bioelectrical sensor including biological sensors, bioactive sensors, etc. For example, each of the sensors 63 can include at least one of an accelerometer, gyroscope, heart rate sensor, blood pressure sensor, magnetometer, electrooculography (EOG) sensor, electroencephalography (EEG) sensor, amperometric sensor, blood sugar sensor, light sensor, body temperature sensor, galvanic skin response (GSR) sensor, and combinations thereof. The sensors 63 can be adapted to detect any suitable physiological characteristic of the wearer. For example, the physiological characteristic can include at least one of body position, eye movement, body temperature, heart rate, EEG, skin impedance, and combinations thereof.

Further, in one or more embodiments, the sensors 63 can be adapted to detect one or more environmental or ambient characteristics proximate the wearer of the hearing device 10. For example, such sensors 63 can include at least one of an ambient temperature sensor, barometer, microphone, GPS sensor, moisture/humidity sensor, image sensor (i.e., a camera), and combinations thereof. The sensors 63 can be adapted to detect any suitable environmental characteristic or characteristics, e.g., temperature, moisture/humidity, sound, light intensity, terrain, elevation, ambient oxygen levels, pollutants, and combinations thereof.

The sensors 63 can also be utilized to electrically connect the hearing device 10 to the wearer's body such that the body can be utilized as an antenna for transmitting information to and from the hearing device. Further, one or more sensors 63 can electrically connect the hearing device 10 to one or more additional body-worn devices by sending electromagnetic signals between the devices through the body. For example, for hearing systems that include two hearing devices, one or more sensors 63 can be utilized for communication between the hearing devices through the skull 8 of the wearer, i.e., ear-to-ear communications. Such communication can be utilized to send electromagnetic signals from one device to the other. For example, the wearer can adjust a volume of an acoustic signal provided by the hearing devices by changing the volume on one device, which sends a control signal to the other device that adjusts its volume. Further, in one or more embodiments, sensor data from the one or more sensors 63 can be coordinated between the two hearing devices. For example, an accelerometer disposed in each device can be utilized to determine whether one of the hearing devices has fallen out of the ear of the wearer by indicating an asymmetric response between the two devices.

Operatively connected to the electronic components 40 is the earpiece 80. The earpiece 80 is adapted to be disposed in an ear canal 5 of the ear 4 of the wearer. The earpiece 80 can include any suitable earpiece. Further, the earpiece 80 can be operatively connected to the electronic components 40 using any suitable technique or techniques. For example, the earpiece 80 can be operatively connected to the electronic components 40 by an ear hook 84. The ear hook 84 can be any suitable ear hook. In one or more embodiments, the ear hook 84 can include one or more lumens. Each lumen can provide any suitable information or signal to the earpiece 80 from the electronic components 40. For example, a first lumen 86 can provide acoustic energy from the components 40 to the earpiece 80, and a second lumen 88 can provide electrical energy (e.g., an electrical signal) to the earpiece. In one or more embodiments, one or more wired lumens can provide electrical power or signals to the earpiece 80.

In one or more embodiments, the ear hook 84 can provide acoustical separation of acoustic signals provided by the components 40. For example, in one or more embodiments, the hearing device 10 can include a woofer disposed on or associated with the housing 20 and a tweeter disposed on or associated with the earpiece 80 such that the tweeter is disposed in the ear canal.

Figure 10:
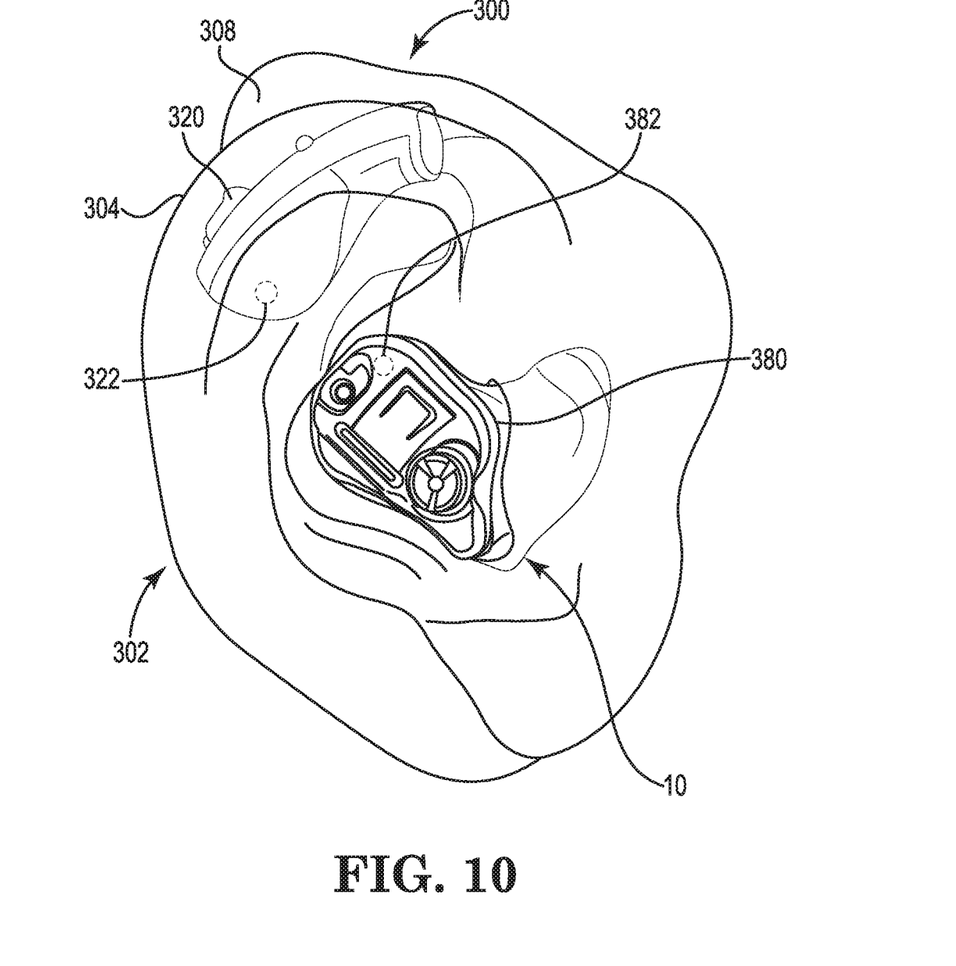
FIG. 10 is a schematic perspective view of another embodiment of a hearing device.

As mentioned herein, the earpiece 80 can be operatively coupled to the housing 20 using any suitable technique or techniques. For example, FIG. 10 is a perspective view of another embodiment of a hearing device 300. All of the design considerations and possibilities regarding the hearing device 10 of FIGS. 1-6 apply equally to the hearing device 300 of FIG. 10. In FIG. 10, the hearing device 300 is shown as being worn by a wearer such that a housing 320 of the device is disposed between a pinna 304 of an ear 302 of the wearer and a skull 308 of the wearer. Further, the hearing device 300 includes an earpiece 380 disposed in at least a portion of an ear canal 310 of the ear 302 of the wearer. The ear 302 is shown as being transparent for illustration purposes.

The housing 320 can include one or more magnetic portions 322 that can be magnetically attracted to one or more magnetic portions 382 of the earpiece 380. This attraction between magnetic portions 322 and 382 can allow the earpiece 380 to be magnetically connected to the housing 320 through the pinna 304 of the wearer. The magnetic portions 322 and 382 can include any suitable magnetic material or materials and be disposed in any suitable location on or within the housing 320 and the earpiece 380 respectively. The magnetic attraction between the housing 320 and the earpiece 380 can hold in place one or both of the housing and the earpiece. Further, the housing 320 and the earpiece 380 can use any suitable technique or techniques to communicate. For example, each of the housing 320 and the earpiece 380 can include an antenna that can be utilized to send and receive information such that one or more electromagnetic signals can be transmitted between the housing and the earpiece.

The various embodiments of hearing devices described herein can be manufactured using any suitable technique or techniques. For example, a semi-custom-made housing can be manufactured utilizing any suitable technique or techniques, e.g., injection molding, 3D printing, etc. Further, for example, computer-aided design software (CAD) modeling can be utilized to form a three-dimensional model of the cleft region of the wearer. In one or more embodiments, the housing can be 3D printed.

The present disclosure can utilize custom 3D CAD modeling, where the housing of the hearing device can be custom fit to the cleft region of the wearer on one or both sides of the wearer's skull. In one or more embodiments, housing customization can be created from a digital scan of an impression of the cleft region of the wearer using a point cloud brought into the housing CAD modeling software. In one or more embodiments, a standard modeling sequence can be utilized that is based on the impression shape and selected style. In one or more embodiments, the cleft region of the wearer can be digitally scanned to provide a model of such region. A completed CAD modeling file can be saved in "stl" file format and provided to a 3D printer. Different 3D printing platforms can be utilized depending upon the material or materials utilized for the housing. For example, a hard resin can be printed layer by layer using stereolithography (SLA) or direct light processing (DLP).

In one or more embodiments, soft silicone can be 3D printed using a thin walled cast methodology, creating a hollow cast with all digital component features. A secondary manual silicone injection process can create the final physical housing. In one or more embodiments, post-processing can include resin removal and curing for hard housings. Soft thin walled casts filled with silicone are cured. After fully curing, the outer casts are cracked and "de-shelled" to uncover the soft earmold. All cast material can then be removed from the housing.

The housing of the hearing device can be fully custom tailored to an individual wearer using any suitable technique or techniques. In one or more embodiments, one or more semi-custom-made housings can be made at one or more preselected sizes, e.g., small, medium, and large sizes utilizing any suitable technique or techniques, e.g., injection molding, 3D printing, etc. For example, one or more housing bodies can be formed based upon one or more preselected sizes, and a custom-made top plate can be designed that can be connected to the one or more premade housing bodies.

Figure 11:
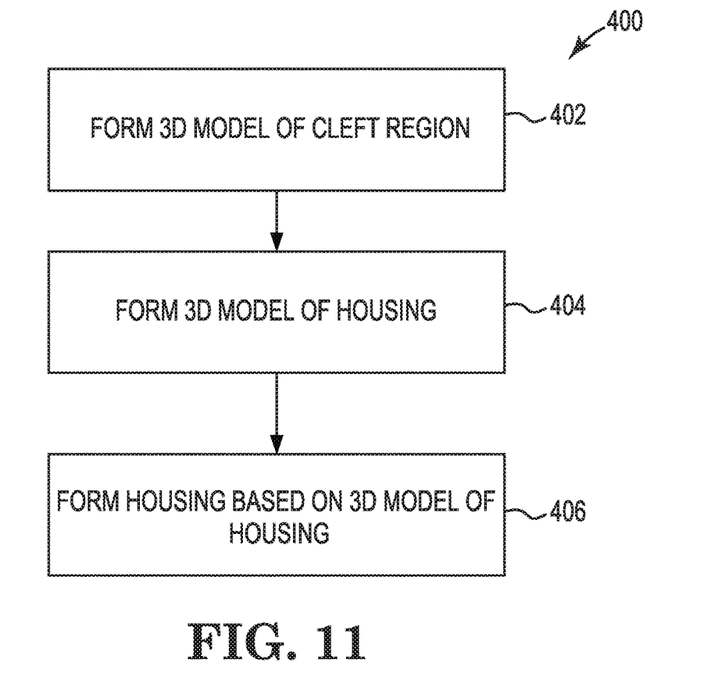
FIG. 11 is a flowchart of one embodiment of a method of making the hearing device of FIG. 1.

FIG. 11 is a flowchart of one embodiment of a method 400 of forming the hearing device 10. While the method 400 is described in reference to the device 10 of FIGS. 1-6, such method can be utilized to form any suitable hearing device.

The method 400 includes forming a three-dimensional model of a cleft region 5 (FIG. 4) between the pinna 4 and the skull 8 of the wearer at 402. Any suitable technique or techniques can be utilized to form the three-dimensional model of the cleft region 5. In one or more embodiments, a mold of the cleft region 5 can be taken using any suitable technique or techniques. Such mold can then be scanned to provide a digital representation of the mold.

In one or more embodiments, the cleft region 5 of the wearer can be scanned using any suitable technique or techniques to provide a three-dimensional digital representation of the cleft region without the need for a physical mold of such region. In one or more embodiments, the three-dimensional model of the cleft region 5 can be formed by scanning the cleft region 5, capturing a selected volume of the cleft region, and isolating the selected volume.

At 404, a three-dimensional model of the housing 20 based upon the three-dimensional model of the cleft region 5 of the wearer can be formed. Any suitable technique or techniques can be utilized to form the three-dimensional model of the housing 20. The three-dimensional model of the housing 20 can include a three-dimensional model of the housing body 22 and a three-dimensional model of the top plate 24. The three-dimensional model of the top plate 24 can be added to the three-dimensional model of the body 22 such that that the top plate model and the body model are integral.

At 406, the housing 20 can be formed from the three-dimensional models of the housing using any suitable technique or techniques, e.g., stereolithography (SLA), fused deposition modeling (FDM), selective laser sintering (SLS), selective laser melting (SLM), electronic beam melting (EBM), laminated object manufacturing (LOM), etc.

In one or more embodiments, the housing 20 can be formed by printing using any suitable printing techniques. In one or more embodiments, the top plate 24 and the housing body 22 can be printed utilizing 3D printing. 3D printing of the top plate 24 and the housing body 22 can include stereo lithographically printing the top plate and the housing. In one or more embodiments, the housing 20 can be 3D printed by utilizing direct light processing.

The housing 20 can be 3D printed using any suitable material or materials. In one or more embodiments, the same material or materials are utilized to print the housing body 22 and the top plate 24. In one or more embodiments, the housing body 22 can include one or more materials that are different from the one or more materials included in the top plate 24.

In one or more embodiments, the housing 20 can be formed by printing a hollow cast that includes a housing body portion. A composition can be disposed within the hollow cast. Any suitable composition can be disposed within the cast, e.g., silicone. The composition can be cured using any suitable technique or techniques to form the housing body 22. The hollow cast can be removed from the housing body 22 utilizing any suitable technique or techniques.

The housing 20 can be trimmed or shaped after the earpiece 12 has been formed to provide a desired final shape and length.

Further, in one or more embodiments, a three-dimensional model of an ear cavity of the wearer can also be modelled to form the earpiece 80 using the same techniques described herein to form the housing 20. The ear cavity can include any suitable portion of the ear canal 5, e.g., the entire ear canal. Similarly, the ear cavity can include any suitable portion of the pinna 4.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A wearable hearing and sensing device comprising:
   a sensor;
   electronic components comprising a controller, a microphone, and an antenna; and
   a housing adapted to be worn on a head of a wearer behind an ear of the wearer in a cleft region that resides between the ear and a skull of the wearer, the housing adapted to fit discretely behind the ear without extending beyond a pinna of the ear, wherein the housing comprises a housing body and an arched top plate connected to the housing body, the housing body comprising a first side surface sized and shaped to conform to a shape of the pinna and a second side surface sized and shaped to conform to a shape of the skull, the arched top plate being sized and shaped to provide space for the sensor and electronic components disposed within the housing but not extending beyond the cleft region to provide a discrete appearance for the wearer, the housing body being sized and shaped to provide consistent placement of the microphone, the antenna, and the sensor with respect to the head of the wearer, the sensor being disposed on at least one of the first or second side surfaces of the housing and electrically coupled to the controller, wherein the sensor is oriented and positioned to assure skin contact between the sensor and the pinna or skin adjacent the skull;

wherein the sensor is adapted to detect a physiological characteristic of the wearer and generate a consistent sensor signal based on the physiological characteristic and the consistent position of the sensor against the skull or pinna, and provide the sensor signal to the controller; and wherein the arched top plate of the housing comprises a curved shape that extends a length of the housing along a housing axis and comprises a first curved shape in the plane orthogonal to the housing axis and a second curved shape in a plane parallel to the housing axis and a bottom edge of the housing body.

2. The device of claim 1, further comprising an earpiece adapted to be disposed in an ear canal of the ear of the wearer, wherein the earpiece is operatively coupled to the electronic components disposed within the housing.

3. The device of claim 2, wherein the housing comprises one or more magnetic portions that can be magnetically attracted to one or more magnetic portions of the earpiece such that the earpiece is magnetically connected to the housing through the pinna of the wearer.

4. The device of claim 1, wherein the sensor comprises at least one of an optical sensor and a bioelectrical sensor.

5. The device of claim 4, wherein the sensor comprises at least one of an electrooculography sensor, electroencephalography sensor, electromyography sensor, galvanic skin response sensor, and amperometric sensor.

6. The device of claim 1, further comprising a second sensor disposed on at least one of the first or second side surfaces of the housing body and adapted to detect a second physiological characteristic of the wearer and generate a second sensor signal based on the second physiological characteristic.

7. The device of claim 6, wherein the sensor is disposed on the first side surface of the housing body and the second sensor is disposed on the second side surface of the housing body.

8. The device of claim 6, wherein the physiological characteristic is different from the second physiological characteristic.

9. The device of claim 1, wherein the arched top plate is connected to the housing body at first and second top edges of the housing body, and the top plate and the first and second side surfaces of the housing body comprise a first material and the first and second top edges of the housing body comprise a second material, the first material comprising a hardness that is greater than a hardness of the second material.

10. The device of claim 1, wherein the arched top plate comprises an outer surface and a notch disposed in the outer surface.

11. The device of claim 10, wherein the arched top plate further comprises a contact pad disposed in the notch of the top plate, the contact pad electrically connected to the electronic components disposed within the housing.

12. A method of forming a hearing device, comprising:
forming a three-dimensional model of a cleft region between a pinna and a skull of a wearer, wherein forming the three-dimensional model of the cleft region comprises:
scanning the cleft region;
capturing a selected volume of the cleft region; and
isolating the selected volume;
forming a three-dimensional model of a housing of the hearing device based upon the three-dimensional model of the cleft region; and
forming a housing of the hearing device based upon the three-dimensional model of the housing, wherein forming the housing comprises:
printing a hollow cast that comprises a housing body portion;
disposing a composition within the hollow cast;
curing the composition to form a housing body of the housing; and
removing the hollow cast from the housing body.

13. The method of claim 12, wherein forming the housing comprises printing the housing.

14. The method of claim 13, wherein printing the housing comprises 3D printing the housing.

15. The method of claim 14, wherein 3D printing the housing comprises stereolithographically printing the housing.

16. The method of claim 12, wherein the three-dimensional model of the housing comprises a three-dimensional model of a housing body of the housing and a three-dimensional model of a top plate of the housing.

17. The method of claim 12, further comprising:
forming a three-dimensional model of an ear cavity of the wearer; and
forming an earpiece based upon the three-dimensional model of the ear cavity.

18. The method of claim 12, wherein forming the housing comprises:
forming a housing body;
forming an arched top plate; and
connecting the arched top plate to the housing body.

19. The method of 18, wherein the arched top plate of the housing comprises a curved shape that extends a length of the housing along a housing axis and comprises a first curved shape in the plane orthogonal to the housing axis and a second curved shape in a plane parallel to the housing axis and a bottom edge of the housing body.

* * * * *